United States Patent [19]
Ackermann

[11] Patent Number: 5,854,667
[45] Date of Patent: Dec. 29, 1998

[54] ELECTROOPTICAL FILTER CARTRIDGE AND A METHOD FOR MANUFACTURING THE SAME

[75] Inventor: Emil Ackermann, Wattwil, Switzerland

[73] Assignee: Oprel AG, Wattwil, Switzerland

[21] Appl. No.: 832,863

[22] Filed: Apr. 4, 1997

Related U.S. Application Data

[63] Continuation of PCT/EP94/03278, Oct. 4, 1994.

[51] Int. Cl.⁶ ........................................................ G02F 1/13
[52] U.S. Cl. .............................. 349/187; 349/58; 349/60; 349/149
[58] Field of Search .................................... 349/187, 149, 349/56, 60, 58

[56] References Cited

U.S. PATENT DOCUMENTS 4,636,037  1/1987  Thomke et al. .......................... 349/149
5,243,453  9/1993  Kawaguchi et al. ..................... 349/149

*Primary Examiner*—William L. Sikes
*Assistant Examiner*—Kenneth Parker
*Attorney, Agent, or Firm*—Pillsbury Madison & Sutro LLP

[57] ABSTRACT

In the invention, an active electrooptical filter cartridge comprises a flat housing (10, 12, 16) forming a closed cavity, which is completely filled with an optical transmissive resin (44, 52, 56, 60, 62) and an active device (14). The active device (14) is completely surrounded and fixed by the resin and comprises as components an LC panel (30, 32) positioned between light-transmissive portions (24, 28) of opposite main walls (10, 16) of the housing, a sensor means (34, 36) for detecting incident light on the filter cartridge, a circuit means (38) for controlling the LC panel (30, 32) in response to an output from the sensor means (34, 36), and a power supply means (40, 42) for operating the active device (14). The filter cartridge can be manufactured with the same dimensions as a passive, darkened filter glass, e.g. for use in welding helmets.

15 Claims, 2 Drawing Sheets

ELECTROOPTICAL FILTER CARTRIDGE AND A METHOD FOR MANUFACTURING THE SAME

This is a Continuation of: International Appln. No. PCT/EP94/03278 filed Oct. 4, 1994.

FIELD OF THE INVENTION

The present invention relates to an electrooptical filter cartridge and to a method for manufacturing such a filter cartridge. The filter cartridge according to the invention is especially, but not exclusively, useful as an active, eye-protection light shutter in a welding helmet or equivalent, replacing the conventional, passive eye-protection filter of darkened class in a welding helmet. The term "welding helmet" is intended to comprise also welder's protective eyeglasses and welder's protective shields.

TECHNOLOGICAL BACKGROUND

A vast majority of today's welding helmets comprise a hinged window plate made of darkened, almost opaque glass. The window is manually flipped down by the welder before starting the welding operation. When the workpiece is to be rearranged, the hinged window must be manually raised. In order to avoid this cumbersome manual lowering and raising of the eye-protective window, welding helmets provided with automatic light-transmission control have been developed based on the use of liquid crystal panels (LC panels). Such automatic helmets are disclosed e.g. in U.S. Pat. No. 3,873,804 (Gordon), U.S. Pat. No. 4,039,254 (Harch) and U.S. Pat. No. 4,240,709 (Hornell).

Gordon teaches the use of photosensitive means mounted on the helmet to respond to a welding arc along with an amplifying circuit for triggering the optical filter from its normal light transmissive condition to its eye-protective, essentially opaque condition.

Both Harch and Hornell teach the use of a multiple-layer protective filter including two or more superposed, parallel electrooptical cells, each of which includes a liquid crystal layer, typically a twisted nematic crystal, sandwiched between parallel glass plates bearing transparent electrodes on their inner surfaces, and polarizers on each side of the electrooptical cells.

An embodiment of the Hornell helmet actually manufactured and sold today includes a plastic shell which is to be placed on the welder's head and which has a front opening wherein a filter cartridge, provided with the above-mentioned automatic light-transmission control feature, is releasably mounted. The cartridge is in the form of a relatively thick, rigid casing having an openable cover on its rear side. An LC panel is mechanically mounted inside the casing together with an on/off switch projecting from the rear side, a sensitivity-adjustment knob also projecting from the rear side, and a replaceable battery accessible through the openable cover. A small hole is provided in the front side of the casing for receiving welding light to be detected by a light sensor also provided inside the casing. Glass plates for protecting the LC panel are arranged on opposite main surfaces of the LC panel, and cover large, rectangular through openings in the front and rear surfaces of the casing.

However, although these automatic welding filters are functionally advantageous compared to passive glass filters, they have a number of drawbacks. First, due to high manufacturing costs, they are normally not competitive with the conventional, passive welding filters made of darkened glass. Second, compared to passive, darkened welding glasses, the known active filter cartridges, as the one used in the Hornell helmet, are heavy and have large dimensions, especially in the thickness direction. Third, known active filter cartridges have a drawback related to the safety of the welder. The components of the known active filter cartridges are easily damaged if, for instance, the cartridge is accidentally dropped. Any such damages to the filter cartridge, e.g. on the LC panel, may result in serious injuries to the welder's eyes during subsequent use.

SUMMARY OF THE INVENTION

Accordingly, it is an object of the invention to provide an improved active, electrooptical filter cartridge, especially for use as a protective eyepiece of a welding helmet, which eliminates the above-mentioned deficiencies of the prior-art, automatic filter cartridges.

A specific object of the invention is to provide an ultra-thin, active, electrooptical filter cartridge having dimensions and an impact resistance comparable to those of a passive, darkened glass filter.

Another object of the invention is to provide an active, electrooptical filter cartridge having no projecting parts.

Still another object of the invention is to provide a cost- and quality-efficient method of manufacturing such an active, electrooptical filter. Specifically, it is an object of the invention to provide a manufacturing method which allows mass production of such cartridges at a competitive price compared to that of passive, darkened glass plates.

Further objects and advantages of the invention will be apparent from the specification.

According to a first aspect of the invention, there is provided an electrooptical filter cartridge, comprising an LC panel for controlling light transmission through the filter cartridge, said filter cartridge being characterised by a flat housing forming a closed cavity, which is completely filled with an optical transmissive resin and an active device, said device being completely surrounded and fixed by the resin and comprising as components said LC panel positioned between light-transmissive portions of opposite main walls of the housing, a sensor means for detecting incident light on the filter cartridge, a circuit means for controlling the LC panel in response to an output from the sensor means, and a power supply means for operating the active device.

According to a second aspect of the present invention, there is provided a method for manufacturing an electrooptical filter cartridge, said method being characterised by the steps of:

forming an open, flat cavity comprising a frame and a bottom wall, filling the cavity completely with an optical transmissive resin and an active device, so that the latter is completely surrounded by the resin, said active device comprising as components an LC panel positioned in parallel with the bottom wall for controlling light transmission through the filter cartridge, sensor means for detecting incident light on the filter cartridge, a circuit means for controlling the LC panel in response to an output from the sensor means, and a power supply means for operating the active device, closing the cavity by sealingly connecting a top wall to the frame, the LC panel being positioned between light-transmissive portions of the bottom and top walls, and curing said resin for fixing the components of the active device in the cavity.

Thus, the invention makes it possible to construct an integrated, ultra-thin, compact, active electrooptical filter cartridge including the most advanced technology, and also makes it possible to mass produce it at a very competitive price, and yet obtain a superior quality and superior impact resistance of the product compared to known active filter cartridges. Especially, the method according to the invention can be performed in a fully automatic, integrated production line, allowing a production of many thousand units a day.

According to the invention, the outer dimensions of the filter cartridge, especially the thickness, can be made essentially equal to the those of a passive, darkened filter glass. As an illustrative example, an active filter cartridge having a thickness less than 5 mm can easily be manufactured according to the invention. Moreover, since the housing is completely filled with the transmissive optical resin and the active device, the inventive filter cartridge will constitute a compact unit presenting high impact resistance, comparable to that of a passive glass plate.

As to the structure of the inventive filter cartridge, it should also be noted that all the components of the active device, including the circuit board, the power supply source and the light sensors, are embedded in the resin within the cavity and are thus not accessible from outside.

As to the method of manufacturing, it should be noted that the bottom wall serves both as a manufacturing aid on which the resin and the active device is arranged, and as a protective surface of the assembled product.

According to a preferred embodiment of the invention, a circuit board of the circuit means is provided with integrated holes, the sensor means being mounted on said circuit board for receiving the incident light through said holes. The side walls of the holes will then have a light-shielding effect on such light which is not to trigger the LC panel. Thus, an effective angular-selective detection of the incident light is obtained without any projecting parts from the filter cartridge.

The above and other preferred features of the invention are stated in the claims and will be apparent from the following description.

DESCRIPTION OF A PREFERRED EMBODIMENT

A preferred embodiment of a filter cartridge according to the invention, and a method for manufacturing the same, will now be described with reference to the accompanying drawings, in which.

Figure 1:
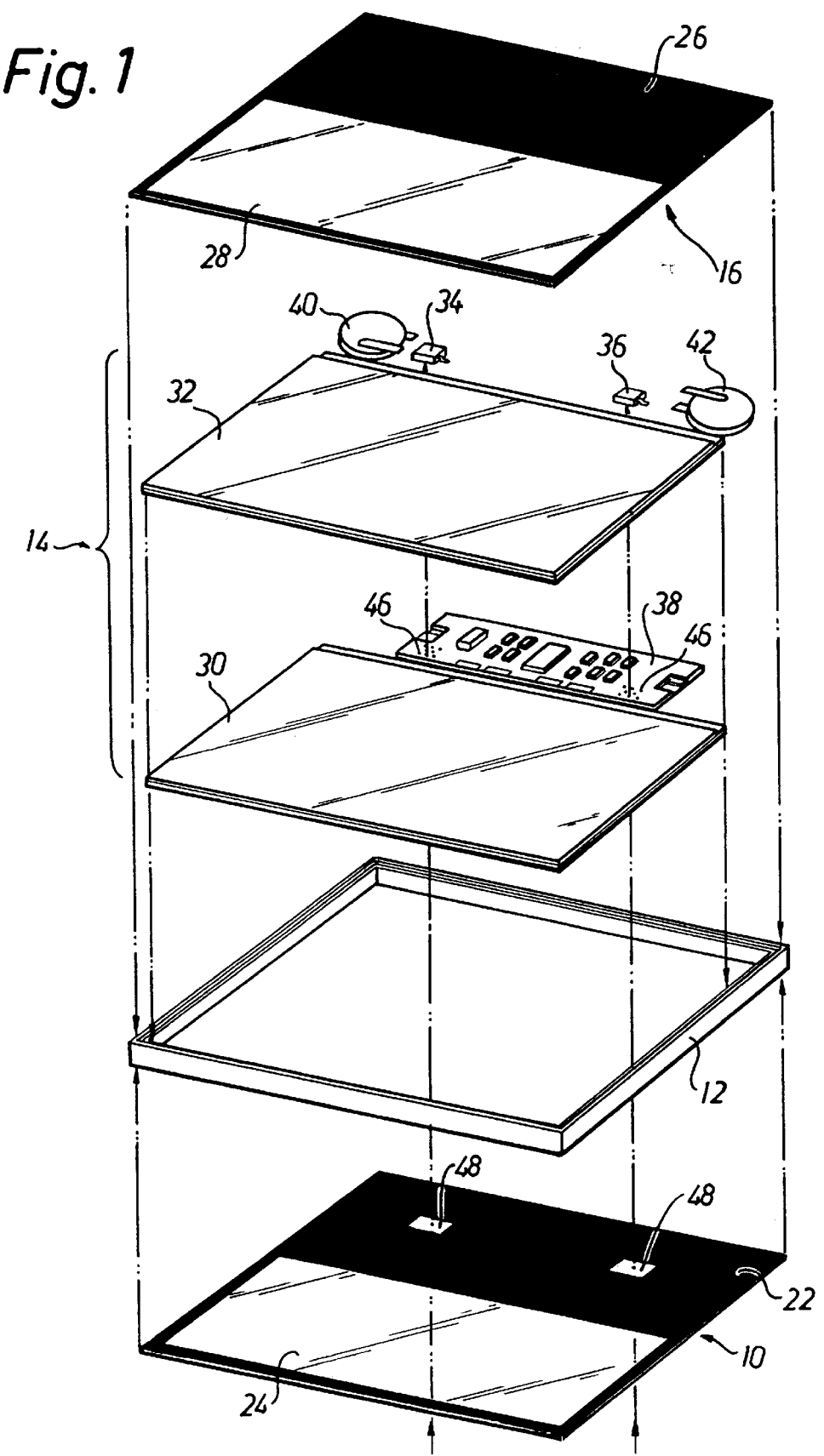
FIG. 1 is an isometric, exploded view of a preferred embodiment of a filter cartridge according to the invention, showing the individual parts of the cartridge, except the optical resin.

Referring now to the drawings wherein like reference numerals refer to like elements, FIG. 1 shows the individual parts of an electrooptical filter cartridge according to a preferred embodiment of the invention, comprising: a rectangular front main wall 10 made of a light-transmissive plastic foil material; a more rigid rectangular frame 12 made of a plastic material of a thicker dimension than the foil 10; an active device generally referred to by reference numeral 14; and a rear main wall 16 essentially identical with the front main wall 10.

Figure 3:
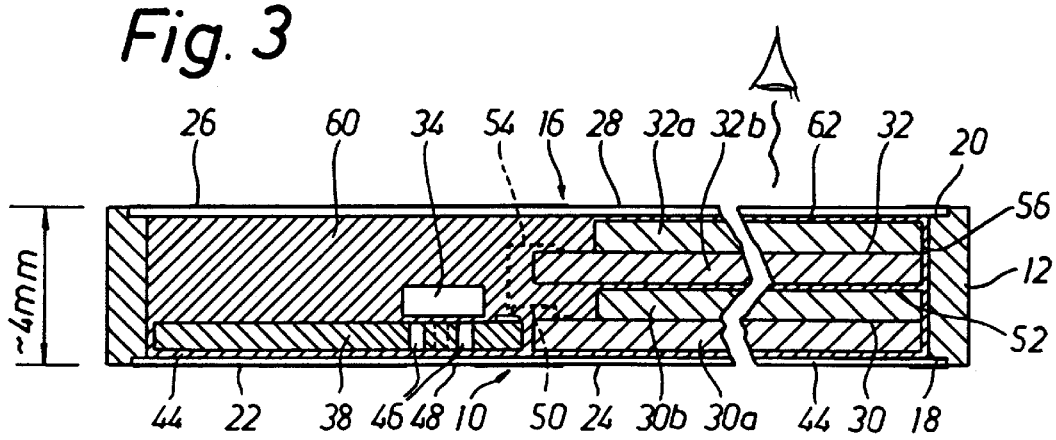
FIG. 3 is a cross-sectional view along the lines III—III in FIG. 2. This figure also illustrates the optical resin.

In the embodiment shown, the highly transparent plastic foils 10, 16 each have a thickness of about 0.2 mm, while the frame 12 has a height of about 4 mm. In the assembled filter cartridge, the front and rear foils 10, 16 are mounted in peripheral recesses 18, 20 provided in the bottom and top surfaces of the frame 12, as best illustrated in FIG. 3. The completely closed housing thus formed by the two rolls 10, 16 and the frame 12 presents an outer thickness of about 4 mm. The lateral dimensions of the filter cartridge may, by way of example only, be in the order of 8×10 cm.

As shown in FIG. 1, the inner surface of the front foil 10 is provided with a printed layer 22 of a light-blocking material, such as a dark-coloured layer, partly covering the front foil 10, whereby the remaining non-darkened area of the front foil 10 defines a light-transmissive, rectangular window portion 24. Similarly, the inner surface of the transparent rear foil 16 is provided with a printed layer 26 of a light-blocking material partly covering the rear foil 16, defining a corresponding light-transmissive window portion 28. These printed layers 22, 26 absorb UV and IR light as well as visible light.

In the illustrative embodiment shown in FIG. 1, the active device 14 comprises as components a 3.8-mm-thick liquid crystal panel (LC panel) made of two superposed 1.8mm-thick electrooptical cells (EO cells) 30, 32, two light sensors 34, 26 for detecting incident welding light, an electronic control circuit board 38 for controlling the LC panel 30, 32 between different light transmission conditions in response to the incident welding light detected, and power supply means in the form of two flat batteries 40, 42.

Each EO cell 30, 32 comprises, as known in the art, a liquid crystal layer (not shown) sandwiched between two parallel glass plates 30a, 30b, 32a, 32b (FIG. 2), transparent electrode layers (not shown) provided on the inner surfaces of the glass plates, and polarizers (not shown) at the outer surfaces of the glass plates. A voltage applied between each electrode pair is controlled by the control circuit board 38 in response to the incident light for changing the transmission of the LC panel between a high-transmissive condition, when no welding light is detected, and an eye-protective low-transmissive condition, when welding light is detailed. The implementation and operation of such a double-celled LC panel 30, 32 and its control circuit 38 will be apparent to a man skilled in the art and, therefore, need no further detailed explanation. Reference can be made e.g. to the U.S. patents mentioned above.

A method for assembling the components shown in FIG. 1 will now be described with reference to the drawings.

STEP 1

Each of the transparent front and rear foils 10, 16 is provided with a printed coloured layer, forming light-blocking areas and limiting the light-transmissive window portions 24, 28. Different colours can be used for these printed layers, and any suitable printing technique can be used. Except the light-blocking function, the printed layers can be used for the purposes of company logos, brand names, etc.

Optionally, the outer surfaces of the front and rear foils 10, 16 can be provided with scratch-resistant coatings (not shown).

STEP 2

The front foil 10 is positioned with its printed light-blocking layer facing upwards, whereupon the frame 12 is glued along the inner periphery of the front foil 10. An open, flat cavity is thus formed. The optical transmissive resin later used inside the cavity can be used also for binding the frame 12 to the front foil 10. The height of the frame 12 will normally be about equal to the thickness of the LC panel 30+32.

STEP 3

Figure 2:
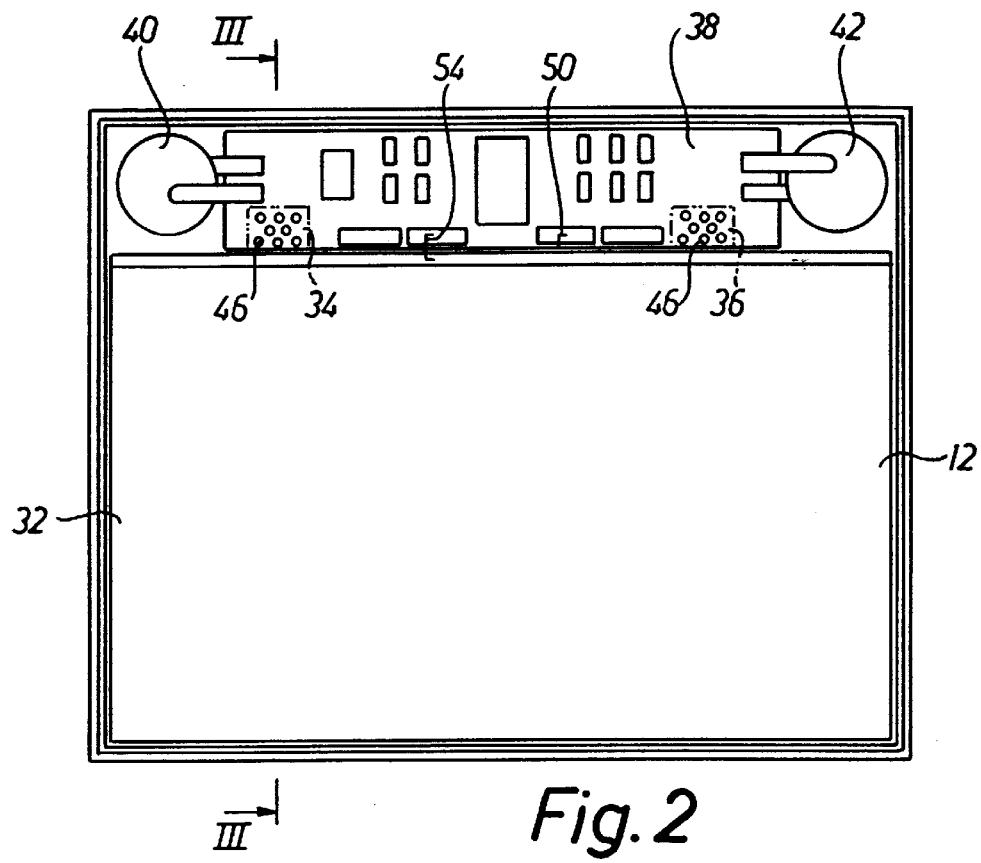
FIG. 2 is a schematic top view of the embodiment in FIG. 1 in its assembled condition.

The electronic control circuit board 38 is fitted into the cavity, resting directly on the front foil 10 or on inwardly-extending notches integrally formed with the frame 12 for positioning purposes. If the circuit board 38 is to be placed directly on the front foil 10, a thin layer 44 of the optical transmissive resin is applied in advance on the front foil 10. Then, the remaining, non-transmissive components of the active device 14, i.e. the two light sensors 34, 36 and the two batteries 40, 42, are fitted into the cavity and soldered to the circuit board 38, as indicated in FIGS. 2 and 3.

In the preferred embodiment, the light sensors 34, 36 are fixedly connected directly on the rear side of the circuit board 38 at locations presenting small holes 46 through the circuit board 38. Thus, light sensitive front surfaces of the sensors 34, 36 will be facing the front foil 10 and receive incident welding light via the thin resin layer 44 and non-darkened openings 48 in the printed colour frame 22. These openings 48 are best illustrated in FIG. 1. This mounting technique prevents residual light (illumination sources, neighbour welders, sunlight, etc.) from triggering the active device 14, since the holes 46 provide effective shielding against such residual light.

STEP 4

The first EO cell 30 is now glued onto the inner surface of the front foil 10, and for this purpose a thin layer 44 of the optical transmissive resin is first applied, as illustrated in FIG. 3. It should be noted that this resin layer 44 covers the entire area of the EO cell 30. The first EO cell 30 is then electrically connected to the circuit board 30, as indicated at 50. The second EO cell 32 is now glued onto the first EO cell 30 by an intermediate layer 52 of the optical transmissive resin, and is thereafter electrically connected to the circuit board 38, as indicated at 54. Obviously, the LC panel 30, 32 has such lateral dimensions that it completely covers the transparent window portions 24, 28 of the front and rear foils 10, 16. However, as illustrated in FIG. 3, there is provided a small gap at 56 between the edges of the LC panel 30, 32 and the inner surface of the frame 12 to be filled with resin.

STEP 5

All redundant space within the cavity is now filled with the optical transmissive resin 60, so that all the components of the active device 14 become completely embedded in the resin. It should be noted that the upper surface of the LC panel 14 will be completely covered by a thin, transparent resin layer 62 and that the above-mentioned gap 56 between the LC panel 14 and the frame 12 will also be filled with resin.

At this stage in the manufacturing process, any curing of the resin in the cavity has normally not yet taken place. Therefore, it is important that the components of the active device 14 fit relatively exactly in the cavity, since the mounting takes place in a somewhat "floating" condition. Optionally, in order to maintain the circuit board 38 in position within the cavity before curing takes place, it is possible to provide notches or the equivalent in the edge of the board 38 for engaging corresponding projections integrated with the inner wall of the frame 12.

STEP 6

The rear foil 16, provided with the printed layer 26, is now glued to the frame 12 and to the top surface of the resin within the cavity. The non-transmissive portions of the active device 14 will now be positioned between the light-blocking areas of the front and rear walls 10, 16, whereas the LC panel 30, 32 will be located between the highly transmissive window portions 24, 28 and sandwiched between the two resin layers 44, 62.

STEP 7

Finally, the resin is cured in order to fix all the components and the front and rear walls.

Thus, in accordance with the present invention, a preferred embodiment of an active filter cartridge and a method for manufacturing the cartridge have been described. It will be obvious to those skilled in the art that modifications are within the scope of the invention and that the appended claims are intended to cover all such modifications.

Thus, the components of the active device 14 may differ from those described. The number of EO cells in the LC panel 14 may be only one or more than two. The power supply means may also include photocells generating electrical power in response to ambient light. The frame 12 may be integrated with the front wall 10. The light sensors 34, 36 may be located outside the circuit board. Further, the described order of the process steps may be altered, e.g. the EO cells may be glued together before placing them in the cavity, the LC panel may be placed within the cavity before the active device 14, some of the components may be electrically connected to each other before they are positioned in the cavity, etc.

I claim:

1. An electrooptical filter cartridge, comprising an LC panel (30, 32) for controlling light transmission through the filter cartridge, characterised by a flat housing (10, 12, 16) forming a closed cavity, which is completely filled with an optical transmissive resin (44, 56, 62) and an active device (14), said device (14) being completely surrounded and fixed by the resin (44, 56, 62) and comprising as components said LC panel (30, 32) positioned between light-transmissive portions (24, 28) of opposite main walls (10, 16) of the housing, a sensor means (34, 36) for detecting incident light on the filter cartridge, a circuit means (38) for controlling the LC panel (30, 32) in response to an output from the sensor means (34, 36), and a power supply means (40, 42) for operating the active device (14).

2. An electrooptical filter cartridge as claimed in claim 1, characterised in that said opposite main walls (10, 16) of the housing are made of a light-transmissive foil material.

3. An electrooptical filter cartridge as claimed in claim 1, characterised in that the opposite main walls (10, 16) present light-blocking areas covering the components (34, 36, 38, 40, 42) of the active device (14), except the LC panel (30, 32).

4. An electrooptical filter cartridge as claimed in claim 3, characterised in that the inner surfaces of the opposite main walls (10, 16) are provided with printed light-blocking layers (22, 26) forming said light-blocking areas.

5. An electrooptical filter cartridge as claimed in claim 1, characterised in that at least one (10) of the main walls (10, 16) of the housing is light-transmissive over an area (48) corresponding to the position of the sensor means (34, 36) in order to allow the incident light to reach the sensor means (34, 36).

6. An electrooptical filter cartridge as claimed in claim 1, characterised in that the circuit means (38) comprises a circuit board provided with integrated holes (46) and in that the sensor means (34, 36) are mounted on said circuit board (46) for receiving said incident light through said holes (46) for obtaining on angular selective detection of the incident light.

7. An electrooptical filter cartridge as claimed in claim 1, characterised in that the thickness of the LC panel (30, 32) essentially equals the internal thickness of the cavity.

8. An electrooptical filter cartridge as claimed in claim 1, characterised in that the thickness of the flat housing (10, 12, 16) is less than 5 mm.

9. A method for manufacturing an electrooptical filter cartridge, characterised by the steps of:

forming an open, flat cavity comprising a frame (12) and a bottom wall (10), filling the cavity completely with an optical, transmissive resin (44, 52, 56, 62) and an active device (14), so that the latter is completely surrounded by the resin (44, 52, 56, 62), said active device (14) comprising as components an LC panel (30, 32) positioned in parallel with the bottom wall (10) for controlling light transmission through the filter cartridge, sensor means (34, 36) for detecting incident light on the filter cartridge, a circuit means (38) for controlling the LC panel (30, 32) in response to an output from the sensor means (34, 36), and a power supply means (40, 42) for operating the active device (14), closing the cavity by sealingly connecting a top wall (16) to the frame (12), the LC panel (30, 32) being positioned between light-transmissive portions (24, 28) of the bottom and top walls (10, 16), and curing said resin (44, 52, 56, 62) for fixing the components (30–42) of the active device (14) in the cavity.

10. A method as claimed in claim 9, characterised in that the step of filling the cavity comprises the substeps of:

providing a layer (44) of said resin on the inner surface of the bottom wall (10), placing the LC panel (30, 32) on said layer (44), placing the other components of the active device (14) inside the cavity, establishing electrical connections (50, 54) between the components of the active device (14), and filling the remaining space of the cavity with said resin (56, 56, 62), including a top layer (62) covering all the components of the active device (14).

11. A method as claimed in claim 9, characterised in that said bottom and top walls (10, 16) are made of light-transmissive foil material.

12. A method as claimed in claim 9, characterised by the further step of providing, on the inner surfaces of the bottom and top walls (10, 16), a light-blocking layer (22, 26) over an area which covers the components (34, 36, 38, 40, 42) of the active device (14), except the LC panel (30, 32).

13. A method as claimed in claim 9, characterised by the further step of providing a UV-IR filter layer on the inner surface of at least one (10) of the bottom wall (10) and the top wall (16).

14. A method as claimed in claim 9, wherein the resulting filter cartridge comprises at least two superposed electrooptical cells (30, 32) forming said LC panel (30, 32), characterised in that the step of filling the cavity comprises the substep of providing an intermediate layer (52) of said resin between adjacent main surfaces of said LC cells.

15. A method as claimed in claim 9, characterised in that the method is performed in a fully automatic, integrated production line.

* * * * *

UNITED STATES PATENT AND TRADEMARK OFFICE
CERTIFICATE OF CORRECTION

PATENT NO.       : 5,854,667

DATED            : December 29, 1998

INVENTOR(S)      : ACKERMAN, Emil

It is certified that error appears in the above-identified patent and that said Letters Patent is hereby corrected as shown below:

On the title page, Item [73],

Change the spelling of the Assignee from "Oprel AG" to --Optrel AG--.

Signed and Sealed this

Twenty-second Day of June, 1999

Attest:

Q. TODD DICKINSON

*Attesting Officer*     Acting Commissioner of Patents and Trademarks